(12) United States Patent
Davis (10) Patent No.: US 8,806,694 B2
(45) Date of Patent: Aug. 19, 2014

(54) CONDUCTOR CLEANING BRUSH ASSEMBLY FOR OVERHEAD ELECTRIC POWER LINES

(71) Applicant: Murray W. Davis, Grosse Pointe Woods, MI (US)

(72) Inventor: Murray W. Davis, Grosse Pointe Woods, MI (US)

(*) Notice: Subject to any disclaimer, the term of this patent is extended or adjusted under 35 U.S.C. 154(b) by 0 days.

(21) Appl. No.: 14/105,508

(22) Filed: Dec. 13, 2013

(65) Prior Publication Data

US 2014/0173842 A1   Jun. 26, 2014

Related U.S. Application Data

(60) Provisional application No. 61/740,517, filed on Dec. 21, 2012.

(51) Int. Cl.
| | |
|---|---|
| *A46B 15/00* | (2006.01) |
| *A46B 9/00* | (2006.01) |
| *B08B 1/00* | (2006.01) |
| *H02G 1/02* | (2006.01) |
| *H02G 7/16* | (2006.01) |

(52) U.S. Cl.
USPC .................. 15/160; 15/104.04; 15/256.6

(58) Field of Classification Search
USPC .................. 15/88, 104.04, 160, 256.6
See application file for complete search history.

(56) References Cited

U.S. PATENT DOCUMENTS

| | | | |
|---|---|---|---|
| 2,303,824 A * | 12/1942 | Comins | 29/76.1 |
| 3,267,507 A * | 8/1966 | Cox | 15/160 |
| 3,861,197 A | 1/1975 | Adler | |
| 4,268,818 A | 5/1981 | Davis et al. | |
| 4,326,316 A * | 4/1982 | Dolenti | 15/246 |
| 4,420,752 A | 12/1983 | Davis et al. | |
| 4,728,887 A | 3/1988 | Davis | |
| 4,746,241 A | 5/1988 | Burbank | |
| 4,806,855 A | 2/1989 | Davis | |
| 4,827,272 A | 5/1989 | Davis | |
| 5,140,257 A | 8/1992 | Davis | |
| 5,232,518 A | 8/1993 | Nath et al. | |
| 5,341,088 A | 8/1994 | Davis | |
| 5,351,359 A * | 10/1994 | Golden | 15/256.6 |
| 6,299,824 B1 * | 10/2001 | Mayr et al. | 266/87 |
| 6,983,508 B2 * | 1/2006 | Saurer | 15/104.04 |
| 7,579,824 B2 | 8/2009 | Rea | |
| 8,022,291 B2 | 9/2011 | Thomsen et al. | |
| 8,320,146 B2 | 11/2012 | Haines et al. | |
| 8,322,332 B2 | 12/2012 | Rogers | |
| 8,628,211 B2 | 1/2014 | Jensen et al. | |
| 2008/0077336 A1 | 3/2008 | Fernandes | |
| 2008/0136403 A1 | 6/2008 | Deck | |
| 2008/0297162 A1 | 12/2008 | Bright | |
| 2010/0085036 A1 | 4/2010 | Banting et al. | |
| 2010/0192975 A1 * | 8/2010 | Schweikert | 134/6 |
| 2011/0308566 A1 | 12/2011 | Johnson | |
| 2012/0152346 A1 | 6/2012 | Yang et al. | |
| 2013/0179079 A1 | 7/2013 | Lancaster | |

FOREIGN PATENT DOCUMENTS

| | | |
|---|---|---|
| CN | 202041573 | 11/2011 |
| JP | 2003-61752 | * 3/2003 |

* cited by examiner

*Primary Examiner* — Mark Spisich
(74) *Attorney, Agent, or Firm* — Carlson, Gaskey & Olds, P.C.

(57) ABSTRACT

An electric power line conductor cleaning brush assembly includes a tubular housing having a longitudinal opening. A multitude of open disc brushes having bristles are located within an interior of the tubular housing and normal to the tubular housing.

13 Claims, 9 Drawing Sheets

CONDUCTOR CLEANING BRUSH ASSEMBLY FOR OVERHEAD ELECTRIC POWER LINES

CROSS-REFERENCE TO RELATED APPLICATIONS

The application claims priority to U.S. Provisional Application No. 61/740,517 which was filed on Dec. 21, 2012.

BACKGROUND

The present disclosure relates to a brush assembly for cleaning an electric power line conductor. In order to properly attach an electrically conducting device to an electric power line, the electric power line must first be cleaned to remove oxide or debris from the electric power line. Occasionally, the brush assembly will be attached to a hotstick. A hotstick is generally used when a utility worker, such as a lineman, is working on a live energized high-voltage electric power line conductor.

When cleaning an electric power line, it is important not to damage the line by scratching or gouging the conductor or an individual strand that forms the conductor. When the conductor or a strand of the conductor is damaged, it can result in corona discharges forming in that portion of the line which can cause audible noise, radio interference, and television interference.

SUMMARY

An electric power line conductor cleaning brush assembly includes a tubular housing having a longitudinal opening. A multitude of open disc brushes having bristles are located within an interior of the tubular housing and normal to the tubular housing.

These and other features of the disclosed examples can be understood from the following description and the accompanying drawings, which can be briefly described as follows.

DETAILED DESCRIPTION

Figure 11:
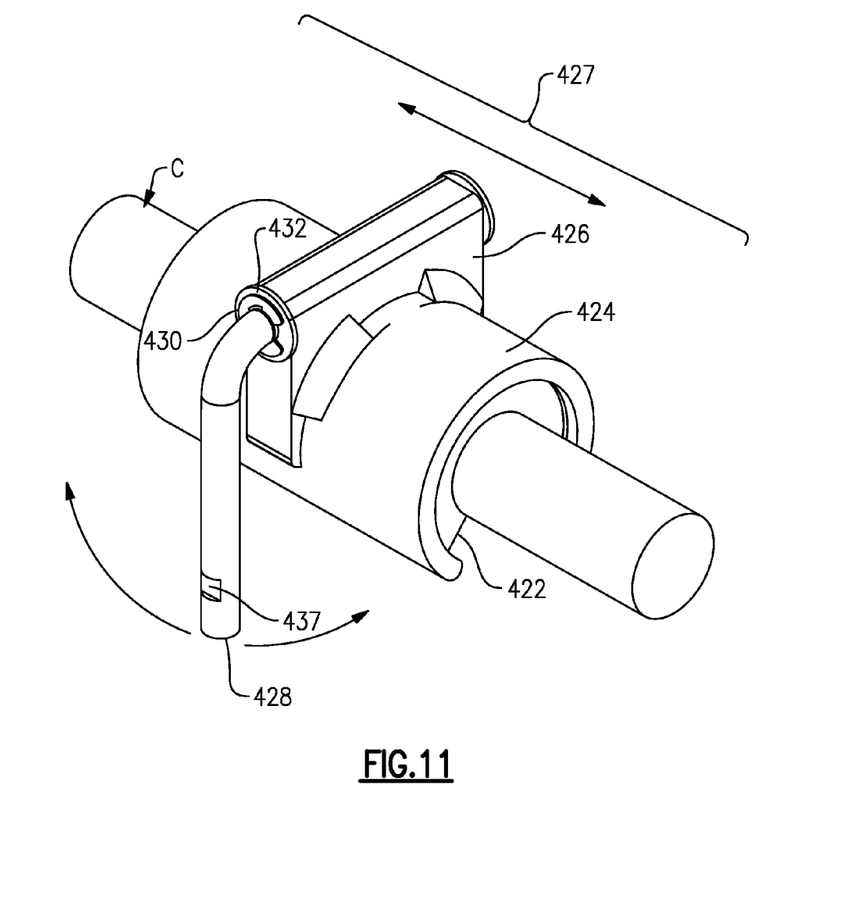
FIG. 11 illustrates the brush assembly of FIG. 10 located on a conductor.

It is very important that all oxides be removed from the surface of either copper or aluminum line conductors C (FIG. 11). Removing oxides from the conductors C allows devices 100, such as conductor temperature measuring devices to properly contact the conductor C to accurately measure the temperature of the conductor C. Additionally, removing oxide allows devices to be attached to the conductor C to be properly grounded to the conductor C.

Figures 1, 2:
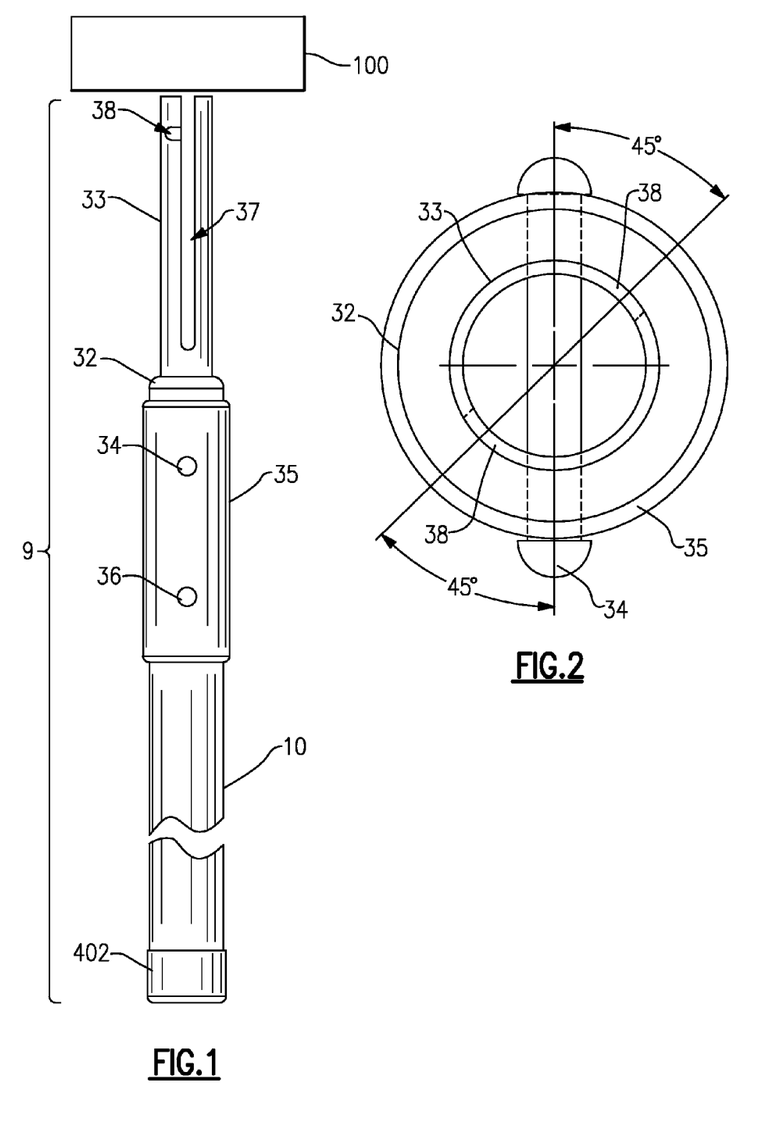
FIG. 1 illustrates a hotstick assembly.
FIG. 2 illustrates an enlarged top view of the hotstick assembly of FIG. 1.

FIG. 1 illustrates a hotstick driver assembly 9 including a lead screw driver 33, a hotstick driver coupling 32, a rivet 34, a hotstick sleeve 35, a pin 36, a tubular fiberglass hotstick 10 and rubber end cap 402. The hotstick 10 rests on the bottom of the hotstick driver coupling 32. The lead screw driver 33 and the hotstick driver coupling 32 are each fastened to the hotstick sleeve 35 by the rivet 34 and the hotstick sleeve 35 is attached to the hotstick 10 with the pin 36. The lead screw driver 33 includes a long narrow vertical slot 37.

The full length of the fiberglass portion of the hotstick 10 including a rubber end cap 402 depends on the operating voltage of a conductor C (FIG. 11) and the specific work rules of different electric utilities whose lineman work on energized conductors C. The full length chosen provides a safe working clearance between the hands of the linemen who may be wearing rubber gloves and holding the hotstick 10 while performing maintenance on or around the energized conductor C.

A keyhole horizontal slot 38 is cut as a small arc of 45 degrees (See FIGS. 1 and 2) beginning at the center of the vertical slot 37 on the front left side and ending on the back right side of the lead screw driver 33 near the top.

At the bottom of the hotstick 10 is the rubber end cap 402 which fits over the outside of the hotstick 10 which is normally filled internally with an electrically insulating foam which prevents water from condensing on the inside of the hotstick 10.

Figures 3, 4:
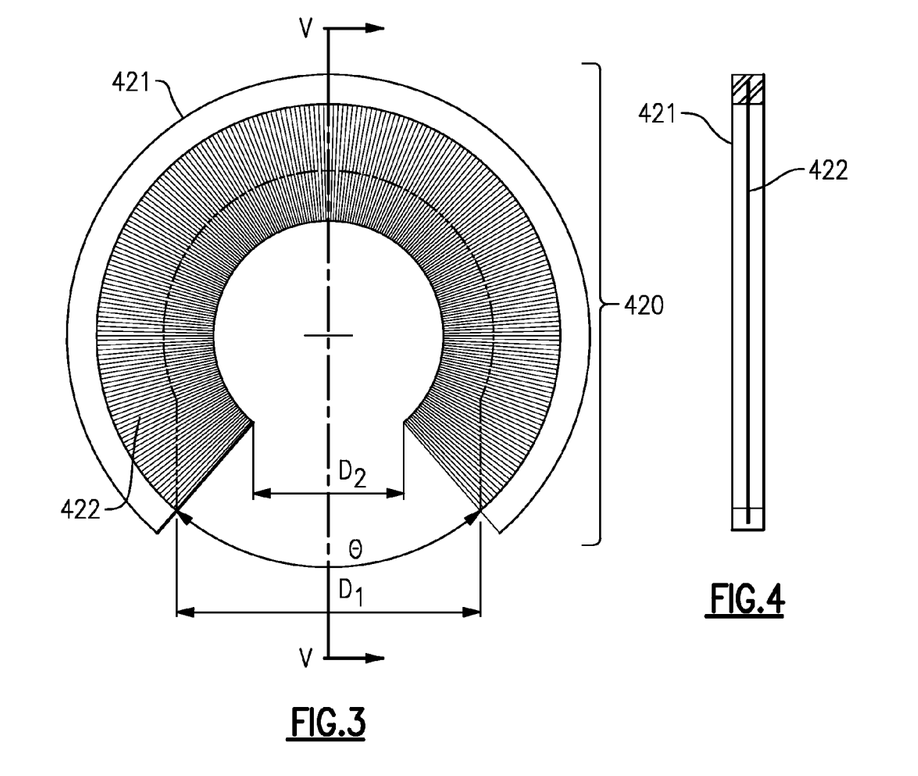
FIG. 3 illustrates a front view of an inside disc brush element.
FIG. 4 illustrates a cross-sectional view of the inside disc brush element taken along line V-V of FIG. 3.
Figure 10:
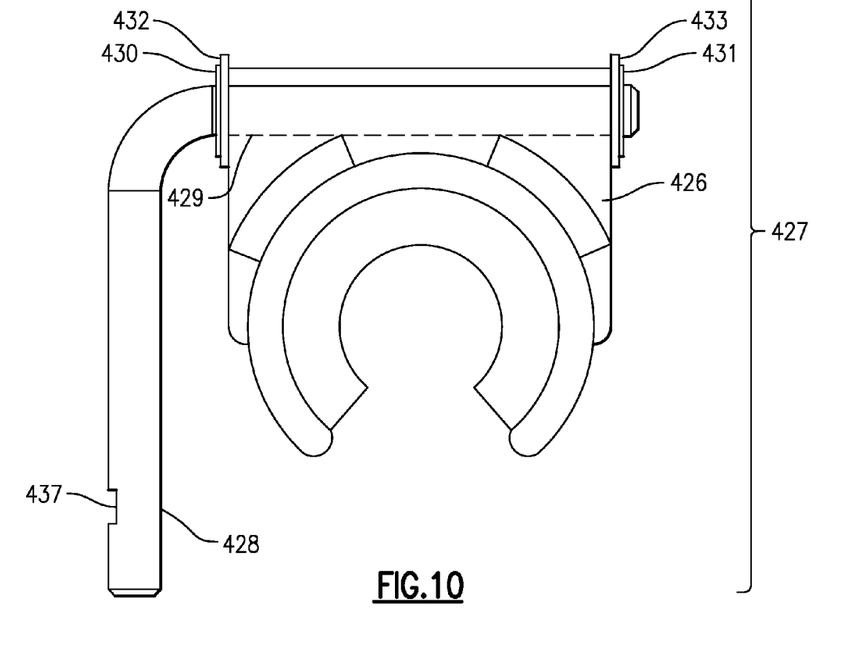
FIG. 10 illustrates a right side view of a conductor cleaning brush assembly.

FIGS. 10 and 11 illustrate an example brush assembly 427 for removing oxides on the conductor C. The brush assembly 427 includes an inside disc brush element 420 as shown in FIG. 3. The inside disc brush element 420 is made as one continuous horizontal strip with a "U" shaped channel 421 crimped over closely spaced wire bristles 422 and bent into a continuous spiral as shown in FIG. 4. The inside disc brush element 420 is made by cutting open and flattening the wire bristles 422 into a complete 360 degree washer shape. The wire bristles 422 are then cut open at an angle θ on the channel 421 to provide an opening at the bottom to accept the largest conductor C without the conductor C coming into direct contact with the channel 421. Only the wire bristles 422 come in contact with the conductor C.

The brush assembly 427 of FIG. 10 must be able to clean conductors C ranging from a diameter of 0.162 inches (4.11 mm) to a diameter of 1.10 inches (27.94 mm) for distribution (low voltage) conductors C. However, for conductors C used with transmission lines, the brush assembly 427 must clean from 1.10 inch diameter up to 2.00 inch (50.8 mm) diameter.

The inside disc brush element 420 has a dimension $D_1$ shown in FIG. 3, which is larger than the largest diameter conductor C to be cleaned, so it is easy to place the brush element over the top of the conductor C. The inside disc brush element 420 also has a dimension $D_2$ which is approximately 60 percent of the diameter of the largest conductor C so the wire bristles 422 near the bottom hold the brush assembly 427 in place on the conductor C.

Figure 5:
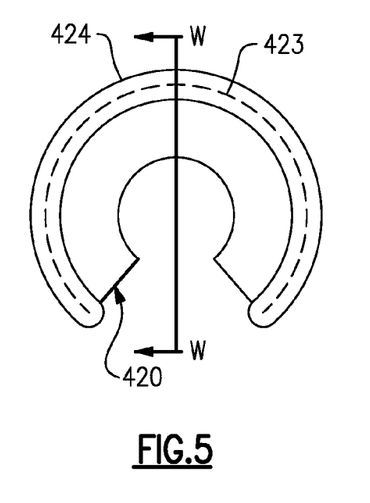
FIG. 5 illustrates a right end view of a slotted tubular housing.
Figure 6:
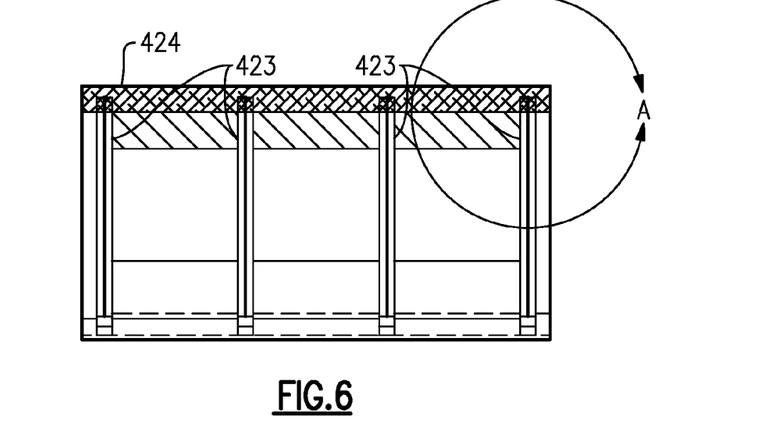
FIG. 6 illustrates a cross-sectional view taken along line W-W of FIG. 5.
Figure 7:
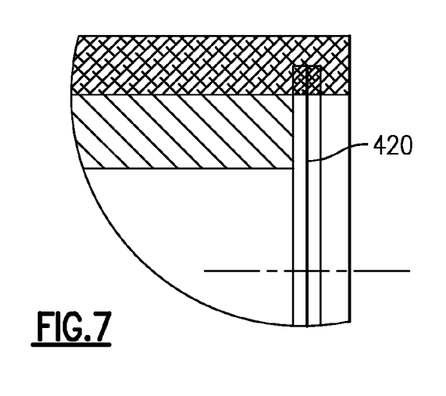
FIG. 7 illustrates an enlarged view of Section A of FIG. 6.

The inside disc brush elements 420 are snapped into semi-circular slots 423 made in a slotted tubular housing 424 as shown in FIGS. 5-7. Each of the inside disc brush elements 420 snap into a corresponding semi-circular slot 423. Although four slots 423 are shown, additional slots 423 can be added along the slotted tubular housing 424. The brush assembly 427 cleans at least the top 180° of the conductor C without rotating the brush assembly 427. The brush assembly 427 cannot cause deep scratches or gouges in the surface of the conductor C, or strands of the conductor C during use or the damage could cause severe corona discharges on high voltage conductors.

Figure 8:
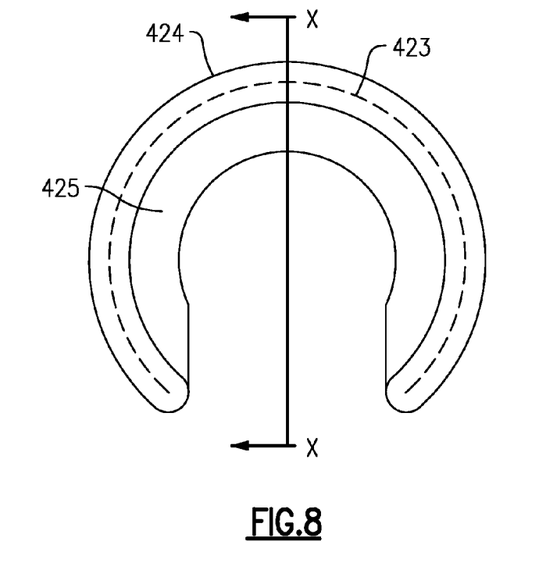
FIG. 8 illustrates a right end view of a rider.
Figure 9:
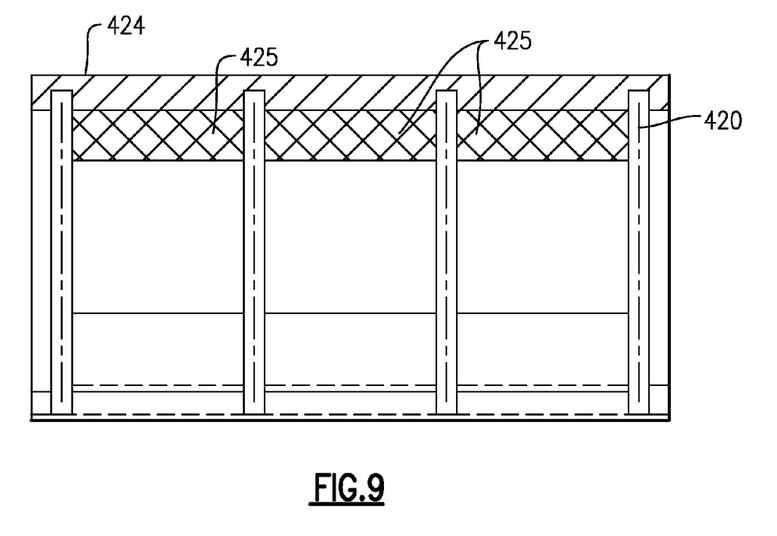
FIG. 9 illustrates a cross-sectional view taken along line X-X of FIG. 8.

To prevent the wire bristles 422 from becoming pushed down and bent over due to extensive use of the brush assembly 427 on conductors C, 'U' shaped riders 425 are placed between each inside disc brush element as shown in FIGS. 8 and 9. The riders 425 are made of a material which does not scratch the conductor C and also prevents the conductor C from coming in contact with the channels 421 which are seated in the slots 423 and are crimped around the wire bristles 422. The riders 425 are fastened to the inside wall of the tubular housing 424, and between slots 423 so the inside disc brush elements 420 can easily be snapped out of the slots 423 and replaced.

A top of the tubular housing 424 is attached to a yoke 426 placed midway between the ends of the tubular housing 424 as shown in FIGS. 10 and 11. Because it is necessary to push the assembly 427 in a back and forth motion on top of the conductor C, a "J" shaped arm 428 is fitted into a hole 429 at the top of the yoke 426 and is free to rotate as illustrated in FIG. 11. The 'J' shaped arm 428 is kept from moving end to end in the hole 429 by two retaining rings 430 and 431 which fit into their respective grooves in the 'J' shaped arm 428 on each side of the yoke 426. Teflon washers 432 and 433 are placed on the 'J' shaped arm 428 at the ends of the hole 429 in the yoke 426 and between each retaining ring 430 and 431 as shown in FIG. 10.

Figure 12:
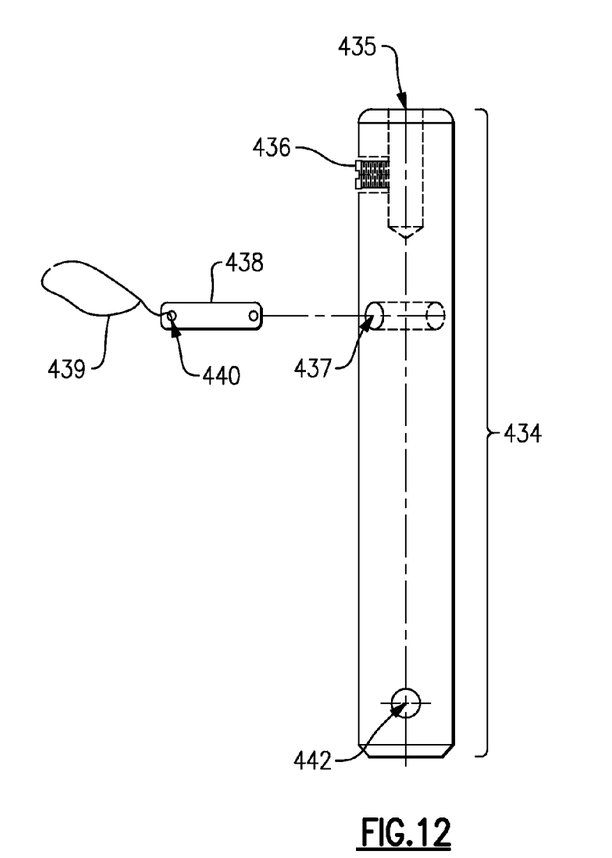
FIG. 12 illustrates a right side view of a hotstick driver adapter.

Since the brush assembly 427 is to be pushed back and forth by the lineman on top of the energized conductor C using the hotstick assembly 9 of FIG. 1, then an adapter 434 is required to attach the "J" shaped arm 428 of FIG. 10 to the lead screw driver 33 of FIG. 1. The adapter 434 is illustrated in FIG. 12. The adapter 434 includes a vertical hole 435 drilled in a top of the adapter 434 and a set screw 436 which is tightened down into a flat milled face 437 on the "J" shaped arm 428 to prevent the "J" shaped arm 428 from rotating when the brush assembly 427 is pushed along the conductor C.

Figure 13:
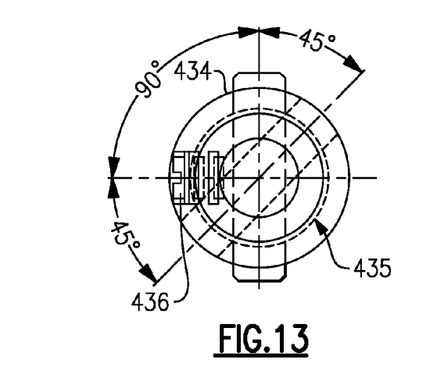
FIG. 13 illustrates an enlarged top view of the hotstick driver adapter of FIG. 12.
Figure 14:
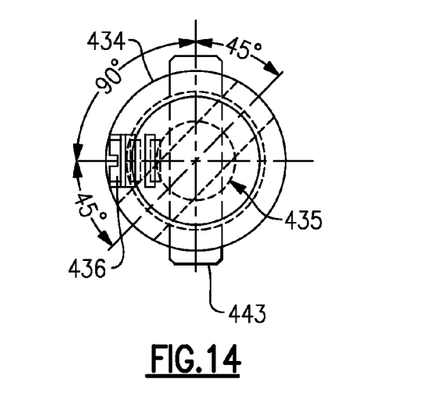
FIG. 14 illustrates an enlarged bottom view of the hotstick driver adapter of FIG. 12.

Below the vertical hole 435 is another hole 437 drilled at a 45 degree angle as viewed in the top view of the adapter 434 of FIG. 13. The angle of the hole 437 matches the arc of the keyhole horizontal slot 38 of the lead screw driver 33 in FIG. 1. A ball detent pin 438 is inserted into the hole 437 after the adapter 434 is slid into the lead screw driver 33. A bail 439 is attached to a small hole 440 at the other end of the ball detent pin 438. The purpose of the bail 439 is to prevent the ball detent pin 438 from being lost when the bail 439 is installed around a base of the adapter 434. Near the bottom of the adapter 434 is a hole 442 through which a small dowel pin 443 is pressed permanently into the hole 442 and the small dowel pin 443 extends beyond the outside circular surface of the adapter 434 on both sides as shown in the bottom view FIG. 14 and engages a vertical slot 37 (FIG. 1).

Figure 15:
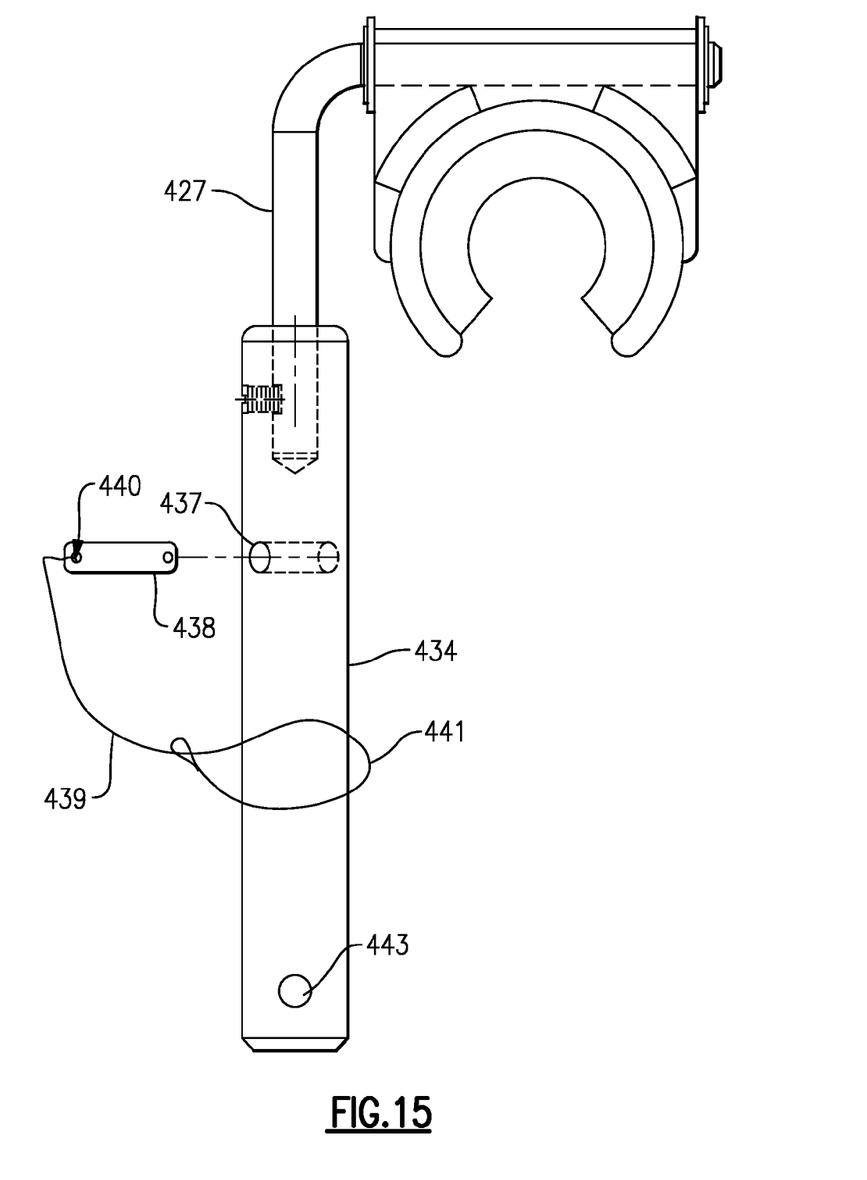
FIG. 15 illustrates a right side view of the brush assembly of FIG. 10 installed on the hotstick driver adapter of FIG. 12.
Figure 16:
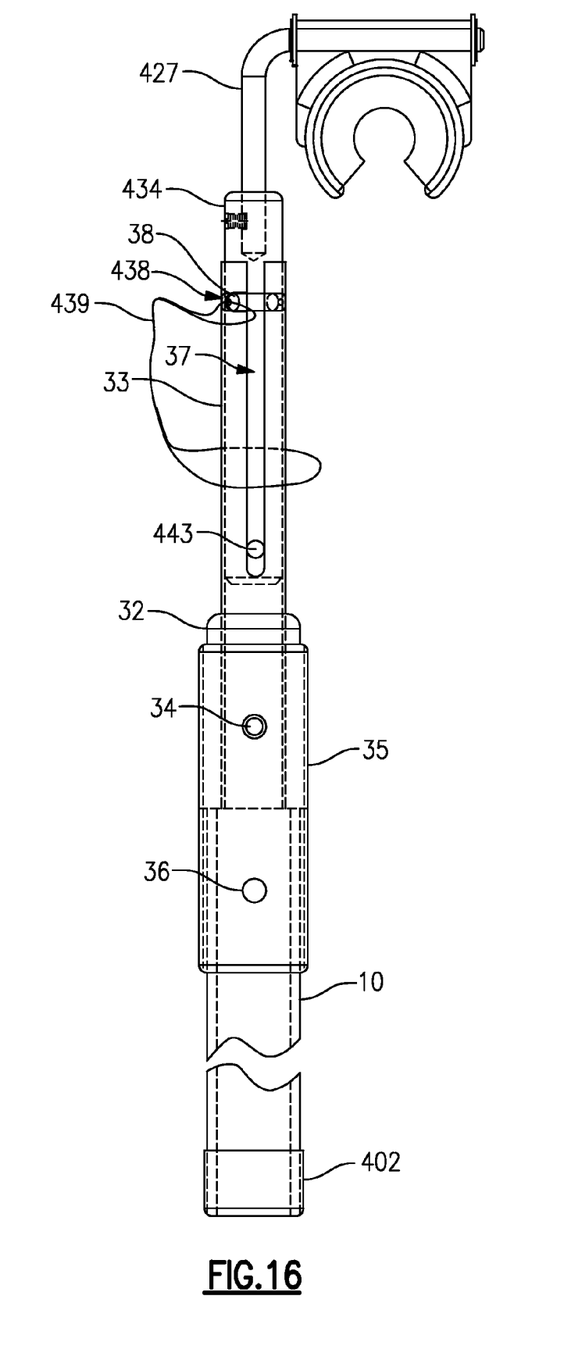
FIG. 16 illustrates the hotstick assembly of FIG. 1 with the brush assembly of FIG. 15 installed on the hotstick driver adapter of FIG. 12.

The FIG. 15 illustrates the bail 439 encircling the adapter 434 and this right side view also shows the brush assembly 427 attached to the adapter 434. The brush assembly 427 and the adapter 434 of FIG. 15 are pushed down inside the lead screw driver 33 of FIG. 1 with the small dowel pin 443 aligned with the vertical slot 37 until the angular hole 437 is aligned with the keyhole slot 38 as illustrated in FIG. 16. Finally, the ball detent pin 438 is pushed through the slot 38 of the lead screw driver 33 and through the hole 437 of the adapter 434. The ball of the detent pin 438 prevents the pin 438 from falling out accidentally while the brush 427 is used to clean the surface of the conductor C.

The preceding description is exemplary rather than limiting in nature. Variations and modifications to the disclosed examples may become apparent to those skilled in the art that do not necessarily depart from the essence of this disclosure. The scope of legal protection given to this disclosure can only be determined by studying the following claims.

What is claimed is:

1. An electric power line conductor cleaning brush assembly comprising:
    a tubular housing including a longitudinal opening; and
    a multitude of open inside disc brushes having bristles located within an interior of the tubular housing and normal to the tubular housing with upside down "U" shaped riders mounted between each of the multitude of open inside disc brushes.

2. The assembly of claim 1 including a yoke mounted perpendicularly on a mid-portion of the tubular housing, a "J" shaped hook rotatably attached to the yoke adjacent a first end and attached to a hotstick on a second end.

3. The assembly of claim 2 wherein the yoke is mounted on top of the mid portion of the tubular housing.

4. The assembly of claim 1 wherein the multitude of open inside disc brushes include a semi-circular inner opening and the multitude of open inside disc brushes are configured to be normal to an axis of an electric power line conductor.

5. The assembly of claim 4 wherein each of the multitude of open inside disc brushes include an opening having a width smaller than a diameter of the semi-circular opening.

6. The assembly of claim 4 wherein the "U" shaped riders are configured to be normal to an axis of an electric power line conductor.

7. The assembly of claim 1 wherein each of the multitude of open inside disc brushes includes multiple bristles crimped together with a "U" shaped channel.

8. The assembly of claim 7 wherein the tubular housing includes a multitude of spaced apart slots for accepting each of the multitude of open inside disc brushes.

9. The assembly of claim 8 wherein the "U" shaped riders are located adjacent an inner diameter of the tubular housing for preventing excessive bending of the bristles of the multitude of open inside disc brushes.

10. The assembly of claim 9 including a yoke mounted perpendicularly on a mid-portion of the tubular housing, a "J" shaped hook rotatably attached to the yoke adjacent a first end and attached to a hotstick on a second end.

11. The assembly of claim 10 wherein the "J" shaped hook is mounted at a bottom vertical end into an adapter which fits inside a tubular vertical slotted driver, the tubular vertical slotted driver is attached to the hotstick and the adapter is held in the tubular vertical slotted driver with a pin inserted through a 45 degree horizontal arc slot near a top of the driver.

12. The assembly of claim 7 wherein each of the multitude of open inside disc brushes with the "U" shaped channel fit inside semicircular slot on an inside of the tubular housing.

13. An electric power line conductor cleaning brush assembly comprising:
- a tubular housing including a longitudinal opening;
- a yoke mounted perpendicularly on a mid-portion of the tubular housing, a "J" shaped hook rotatably attached to the yoke adjacent a first end and attached to a hotstick on a second end; and
- a multitude of open disc brushes having bristles located within an interior of the tubular housing and normal to the tubular housing.

* * * * *